United States Patent [19]

Fontana

[11] Patent Number: 5,426,123
[45] Date of Patent: Jun. 20, 1995

[54] METHOD FOR LOWERING SERUM CHOLESTEROL WITH 1,1,2-TRIPHENYLBUT-1-ENE DERIVATIVES

[75] Inventor: Steven A. Fontana, Martinsville, Ind.

[73] Assignee: Eli Lilly and Company, Indianapolis, Ind.

[21] Appl. No.: 241,262

[22] Filed: May 11, 1994

[51] Int. Cl.$^6$ .................................... A61K 31/135
[52] U.S. Cl. .................................... 514/651
[58] Field of Search .......................... 514/651

[56] References Cited

U.S. PATENT DOCUMENTS 5,047,431  9/1991  Schickaneder et al. ............ 514/651
5,254,594  10/1993  Niikura et al. .................... 514/651

Primary Examiner—Jerome D. Goldberg
Attorney, Agent, or Firm—Steven A. Fontana; David E. Boone; Gerald V. Dahling

[57] ABSTRACT

The present invention provides a novel method of lowering serum cholesterol in humans comprising

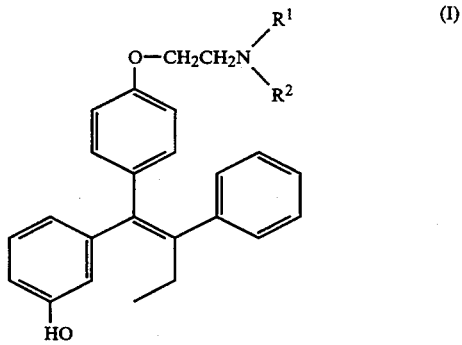

wherein
$R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is a benzyl group, or a pharmaceutically acceptable salt thereof.

3 Claims, No Drawings

METHOD FOR LOWERING SERUM CHOLESTEROL WITH 1,1,2-TRIPHENYLBUT-1-ENE DERIVATIVES

BACKGROUND OF THE INVENTION

The present invention relates to the discovery that a group of 1,1,2-triphenylbut-1-ene derivatives are useful for lowering serum cholesterol in humans.

All mammalian cells require cholesterol as a structural component of their cell membranes and for non-sterol end products. The very property, however, that makes cholesterol useful in the cell membranes, its insolubility in water, also makes it potentially lethal. When cholesterol accumulates in the wrong place, for example within the wall of an artery, it cannot be readily mobilized and its presence leads to the development of an atherosclerotic plaque. Elevated concentrations of serum cholesterol associated with low density lipoproteins (LDL'S) have been demonstrated to be a major contributing factor in the development and progression of atherosclerosis.

Estrogen, particularly when taken orally, lowers plasma levels of LDL and raises those of the beneficial high density lipoproteins (HDL's). Long-term estrogen therapy, however, has been implicated in a variety of disorders, including an increase in the risk of uterine cancer and possibly breast cancer, causing many women to avoid this treatment. Recently suggested therapeutic regimens which seek to lessen the cancer risk, such as administering combinations of progestin and cause the patient to experience unacceptable bleeding. Furthermore, combining progestin with estrogen seems to blunt the serum cholesterol lowering effects of estrogen. The significant undesirable effects associated with estrogen therapy support the need to develop alternative therapies for hyperlipidemia/hypercholesterolemia that have the desirable effect on serum LDL but do not cause undesirable effects.

Attempts to fill this need by the use of other compounds commonly known as antiestrogens, which interact with an estrogen receptor and/or bind with what has been termed the antiestrogen binding site (AEBS) have had limited success, perhaps due to the fact that these compounds generally display a mixed agonist/antagonist effect and are subject to the same adverse effects associated with estrogen therapy. The compound tamoxifen exemplifies this type of antiestrogen compound.

The present invention provides methods for lowering serum cholesterol levels while mitigating the associated adverse effects of estrogen therapy, particularly, the well known uterotrophic effects caused by estrogen and most antiestrogenic agents. Thus, compounds of formula I provide an effective and acceptable treatment for hyperlipidemia/hypercholesterolemia.

SUMMARY OF THE INVENTION

The present invention relates to a method for lowering serum cholesterol comprising administering to a human in need of treatment an effective amount of a compound of formula I

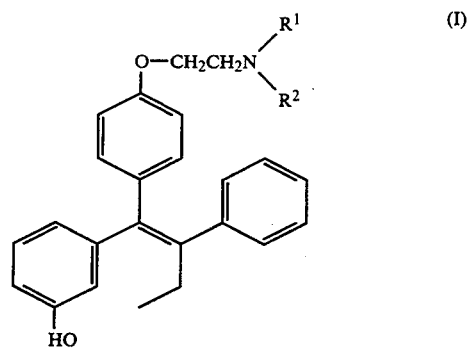

wherein
$R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is a benzyl group, or a pharmaceutically acceptable salt thereof.

DETAILED DESCRIPTION OF THE INVENTION

The present invention concerns a method for lowering serum cholesterol levels in humans.

The methods of this invention are practiced by administering to an individual in need of treatment an effective amount of a compound of formula I

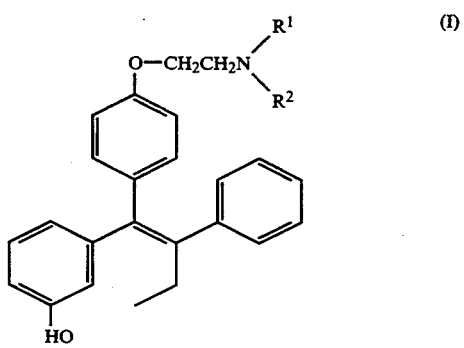

wherein
$R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is a hydrogen group; or a pharmaceutically acceptable salt thereof.

Compounds of formula I are known in the art and essentially are prepared via the methods described in U.S. Pat. No. 5,047,431, which is herein incorporated by reference.

A preferred formula I compound is that in which $R^1$ and $R^2$ each are methyl. This compound is known as droloxifene which previously has been described as an antiestrogenic agent and is useful for the treatment of hormone-dependent mammary tumors (U.S. Pat. No. 5,047,431), and for the relief of bone diseases caused by the deficiency of estrogen or the like (U.S. Pat. No. 5,254,594).

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of inorganic and, preferrably, organic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, subcrate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the citrate salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts of formula I compounds generally have enhanced solubility characteristics compared to the compound from which they are derived, and thus are often more amenable to formulation as liquids or emulsions.

Once prepared, the free base or salt form of formula I compounds can be administered to an individual in need of treatment for the method herein described. The following non-limiting test example illustrates the methods of the present invention.

TEST PROCEDURES

General Preparation Procedure

In the examples illustrating the method of the present invention, a post-menopausal model is used in which effects of different treatments upon circulating lipids are determined.

Seventy-five day old female Sprague Dawley rats (weight range of 200 to 250 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room is 12 hours light and 12 hours dark.

Dosing Regimen Tissue Collection. After a one week acclimation period (therefore, two weeks post-OVX) daily dosing with test compound is initiated. 17 α-ethynyl estradiol, tamoxifen, and the test compounds are given orally, unless otherwise stated, as a suspension in 20% cyclodextrin. Animals are dosed daily for 4 days. Following the dosing regimen, animals are weighed and anesthetized with a ketamine: Xylazine (2:1, V:V) mixture and a blood sample is collected by cardiac puncture. The animals are then sacrificed by asphyxiation with $CO_2$, the uterus is removed through a midline incision, and a wet uterine weight is determined.

Cholesterol Analysis. Blood samples are allowed to clot at room temperature for 2 hours, and serum is obtained following centrifugation for 10 minutes at 3000 rpm. Serum cholesterol is determined using a Boehringer Mannheim Diagnostics high performance cholesterol assay. Briefly the cholesterol is oxidized to cholest-4-en-3-one and hydrogen peroxide. The hydrogen peroxide is then reacted with phenol and 4-aminophenazone in the presence of peroxidase to produce a p-quinonoe imine dye, which is read spectrophotemetrically at 500 nm. Cholesterol concentration is then calculated against a standard curve. The entire assay is automated using a Biomek Automated Workstation. Lowering of serum cholesterol versus overiectomized animals and reduced uterine weight versus 17 α-ethynyl estradiol and/or tamoxifen, indicates the compounds used in the methods of the present are of potential for beneficially lowering serum cholesterol.

For the method of the present invention, compounds of Formula I are administered continuously, from 1 to 4 times daily.

As used herein, the term "effective amount" means an amount of compound of the method of the present invention which is capable of lowering serum cholesterol. The specific dose of a compound administered according to this invention will, of course, be determined by the particular circumstances surrounding the case including, for example, the compound administered, the route of administration, the state of being of the patient, and the severity of the pathological condition being treated. A typical daily dose will contain a nontoxic dosage level of from about 0.25 mg to about 400 mg/day of a compound of the present invention. Preferred daily doses generally will be from about 1 mg to about 20 mg/day.

The compounds of this invention can be administered by a variety of routes including oral, rectal, transdermal, subucutaneus, intravenous, intramuscular, and intranasal. These compounds preferably are formulated prior to administration, the selection of which will be decided by the attending physician. Typically, a formula I compound, or a pharmaceutically acceptable salt thereof, is combined with a pharmaceutically acceptable carrier, diluent or excipient to form a pharmaceutical formulation.

The total active ingredients in such formulations comprises from 0.1% to 99.9% by weight of the formulation. By "pharmaceutically acceptable" it is meant the carrier, diluent, excipients, and/or salt must be compatible with the other ingredients of the formulation, and not deleterious to the recipient thereof.

Pharmaceutical formulations containing a compound of formula I can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I generally will be administered in a convenient formulation. The following formulation examples only are illustrative and are not intended to limit the scope of the present invention.

FORMULATIONS

In the formulations which follow, "active ingredient" means a compound of formula I, or a salt thereof.

Formulation 1: Gelatin Capsules
Hard gelatin capsules are prepared using the following:

| Ingredient | Quantity (mg/capsule) |
| --- | --- |
| Active ingredient | 0.25–400 |
| Starch, NF | 0–650 |
| Starch flowable powder | 0–50 |
| Silicone fluid 350 centistokes | 0–15 |

The formulation above may be changed in compliance with the reasonable variations provided.

A tablet formulation is prepared using the ingredients below:

| Formulation 2: Tablets | |
| --- | --- |
| Ingredient | Quantity (mg/tablet) |
| Active ingredient | 0.25–400 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–400 mg of active ingredient are made up as follows:

| Formulation 3: Tablets | |
| --- | --- |
| Ingredient | Quantity (mg/tablet) |
| Active ingredient | 0.25–400 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–400 mg of medicament per 5 ml dose are made as follows:

| Formulation 4: Suspensions | |
| --- | --- |
| Ingredient | Quantity (mg/5 ml) |
| Active ingredient | 0.25–400 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

| Formulation 5: Aerosol | |
| --- | --- |
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Formulation 6: Suppositories | |
| --- | --- |
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool. An intravenous formulation is prepared as follows:

| Formulation 7: Intravenous Solution | |
| --- | --- |
| Ingredient | Quantity |
| Active ingredient | 20 mg |
| Isotonic saline | 1,000 mL |

The solution of the above ingredients is intravenously administered to a patient at a rate of about 1 mL per minute.

We claim:

1. A method of lowering serum cholesterol levels, comprising administering to a human in need of treatment an effective amount of a compound of formula (I)

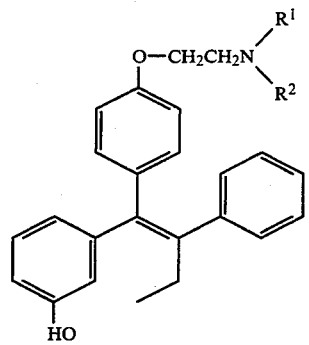

wherein
$R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is a hydrogen; or a pharmaceutically acceptable salt thereof.

2. A method according to claim 1 wherein the compound of formula I is a compound wherein $R^1$ and $R^2$ each are methyl, or a pharmaceutically acceptable salt thereof.

3. A method according to claim 2 wherein said salt thereof is the citrate salt.

* * * * *